United States Patent [19]

Maravetz

[11] Patent Number: 4,919,708
[45] Date of Patent: Apr. 24, 1990

[54] HALOALKYL TRIAZOLINONES AND HERBICIDAL USE THEREOF

[75] Inventor: Lester L. Maravetz, Westfield, N.J.

[73] Assignee: FMC Corporation, Philadelphia, Pa.

[21] Appl. No.: 372,207

[22] Filed: Jun. 26, 1989

Related U.S. Application Data

[63] Continuation of Ser. No. 102,303, Sep. 25, 1987, abandoned, which is a continuation of Ser. No. 825,520, Feb. 3, 1986, abandoned, which is a continuation-in-part of Ser. No. 697,619, Feb. 4, 1985, abandoned, which is a continuation-in-part of Ser. No. 655,960, Sep. 28, 1984, abandoned, which is a continuation-in-part of Ser. No. 541,596, Oct. 13, 1983, abandoned, which is a continuation-in-part of Ser. No. 650,755, Sep. 13, 1984, abandoned, which is a continuation-in-part of Ser. No. 533,013, Sep. 15, 1983, abandoned, which is a continuation-in-part of Ser. No. 666,933, Oct. 31, 1984, abandoned.

[51] Int. Cl.$^5$ .................. A01N 43/36; C07D 249/12
[52] U.S. Cl. ...................................... 71/92; 548/263.2
[58] Field of Search ..................... 71/92; 548/263, 265

[56] References Cited

U.S. PATENT DOCUMENTS

| | | | |
|---|---|---|---|
| 3,213,135 | 10/1965 | Speziale et al. | 560/161 |
| 4,318,731 | 3/1982 | Kajioka et al. | 71/92 |
| 4,398,943 | 8/1983 | Kajioka et al. | 71/92 |
| 4,702,763 | 10/1987 | Maravetz | 71/90 |
| 4,705,557 | 11/1987 | Maravetz | 71/92 |

FOREIGN PATENT DOCUMENTS

| | | | |
|---|---|---|---|
| 696346 | 8/1940 | Fed. Rep. of Germany | 560/161 |
| 57-181069 | 11/1982 | Japan. | |
| 58-225070 | 12/1983 | Japan | 71/92 |

OTHER PUBLICATIONS

Burger, Medicinal Chemistry, p. 1055 (2nd Ed., 1960).
Nuridzhanyan et al., "Acylisocyanates and Their Derivatives", Chem. Abstr. 71:123768e (1969).
Kiemstedt et al., "Reaktionen des (Trifluoroacetyl) Isocyanats," Chemische Berichte 115: pp. 919–925 (1982).
STN International Search Results, American Chemical Society (CAS Online), search conducted 10 Jul. 84, 18 pages.

*Primary Examiner*—David B. Springer
*Attorney, Agent, or Firm*—Robert M. Kennedy; Beverly K. Johnson; Abner Sheffer

[57] ABSTRACT

Herbicidal 1-aryl-1,2,4-triazolin-5(1H)-ones having a haloalkyl group (e.g. $CHF_2$, $CF_3$ or $CClF_2$) attached to the carbon atom at the 3-position of the triazolinone ring.

5 Claims, No Drawings

HALOALKYL TRIAZOLINONES AND HERBICIDAL USE THEREOF

This application is a continuation of application Ser. No. 102,303, filed Sept. 25, 1987, which is a division of application Ser. No. 825,520, filed Feb. 3, 1986, which is a continuation-in-part of application Ser. No. 697,619, filed Feb. 4, 1985, which is a continuation-in-part of application Ser. No. 655,960 filed Sept. 28, 1984 (and its parent application Ser. No. 541,596 filed Oct. 13, 1983); Ser. No. 650,755 filed Sept. 13, 1984 (and its parent application Ser. No. 533,013 filed Sept. 15, 1983); and Ser. No. 666,933 filed Oct. 31, 1984, all abandoned.

This invention relates to herbicidal 1-aryl-4,5-dihydro-1,2,4-triazol-5(1H)-ones having a haloalkyl group on the carbon at the 3-position of the triazolinone ring.

The herbicidal activity of certain 1-aryl-4,5-dihydro-1,2,4-triazol-5(1H)-ones (also known as 1-aryl-$\Delta^2$-1,2,4-triazolin-5-ones) having an alkyl group attached to the carbon at the 3-position of the heterocyclic ring has been described in the patent literature, as discussed below.

British published patent application 2,090,250 discloses herbicidal compounds of the formula

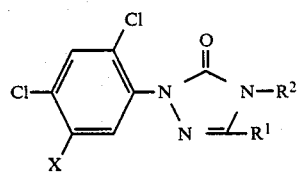

wherein $R^1$ is an alkyl group, $R^2$ is an alkynyl group, a halomethyl group, or a haloethyl group and X is an alkoxy group, an alkenyloxy group, an alkoxyalkoxy group, an alkynyloxy group, a hydroxy group, a halomethyloxy group, or a haloethyloxy group.

Japanese Kokai 107,975 discloses herbicidal compounds of the formula

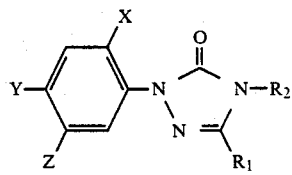

($R_1$ is 1-4C alkyl; $R_2$ is H, 1-4C alkyl, halomethyl or 3-4C alkynyl; X is Cl or F; Y is Cl, Br, OH or $OR_3$; $R_3$ is 1-4C alkyl or benzyl; Z is H, carboxy, cyanomethoxy, $COOR_4$, $COSR_5$ or $CON(R^6)$ ($R^7$); $R_4$ is 1-4C alkyl or 3-4C alkoxyalkyl; $R_5$ is 1-4C alkyl; and $R_6$ and $R_7$ are H, 1-4C alkyl or alkoxy).

U.S. Pat. No. 4,318,731 discloses herbicidal compounds of the formula

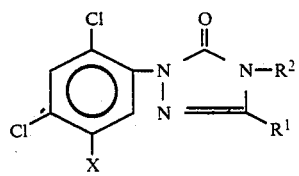

wherein $R^1$ is $C_1$-$C_4$ alkyl; $R^2$ is hydrogen, $C_1$-$C_6$ alkyl or $C_1$-$C_4$ alkenyl; and X is hydroxy, $C_1$-$C_4$ alkyl, $C_1$-$C_6$ alkyloxy, an alkyloxyalkyloxy of which two alkyls may be the same or different and each alkyl is $C_1$-$C_4$, a $C_2$-$C_4$ alkenyloxy, or an alkyloxycarbonylalkyloxy of which two alkyls may be the same or different and each alkyl is $C_1$-$C_4$.

Also, U.S. Pat. No. 4,404,019 discloses herbicidal compounds of the formula

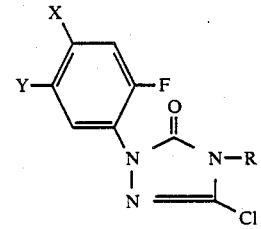

wherein R is a $C_1$-$C_4$ alkyl group, a $C_3$-$C_4$ alkenyl group or a $C_3$-$C_4$ cycloalkyl group, X is a chlorine or bromine atom and Y is a hydrogen atom or a $C_1$-$C_4$ alkoxy group.

Japanese Kokai 60-149,571 discloses herbicidal compounds of the formula

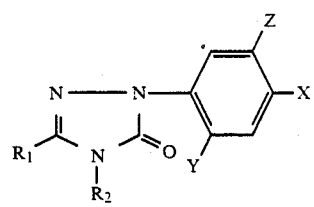

in which $R_1$ is H or alkyl;
$R_2$ is H, alkyl, alkenyl, alkynyl or haloalkyl;
X and Y are halogen;
Z is nitro, amino or

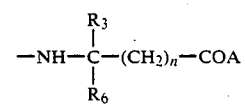

$R_3$ is H or alkyl;
$R_4$ is H or methyl;
n is 0, 1 or 2;
A is $OR_5$, $SR_6$ or $NR_7R_8$;
$R_5$ is H, alkyl, alkenyl or alkynyl;
$R_6$ is alkyl;
$R_7$ and $R_8$ are alkyl, alkoxy, alkenyl, alkynyl, alkenyloxy, alkoxyalkoxy, cycloalkyl, alkylsulphonyl or aryl,
or $NR_7R_8$ form a heterocyclic ring.

The compounds of this invention are herbicidal aryl-4,5-dihydro-1,2,4-triazol-5(1H)-ones (such as those in the prior art, e.g. described above) in which, however, the carbon atom at the 3-position of the triazole ring carries a $C_1$-$C_4$ haloalkyl group whose halogens are selected from F, Cl and Br, particularly a fluoroalkyl (e.g. difluoromethyl) group.

The compounds of the invention are those which have the following formula:

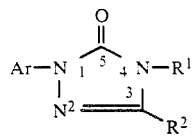

where $R^2$ is said haloalkyl group and $R^1$ may be hydrogen, but preferably is alkyl (e.g. of 1 to 6, preferably 1 to 4, carbon atoms); haloalkyl (e.g. of 1 to 5, preferably 1 to 3, carbon atoms particularly fluoroalkyl); cyanoalkyl (e.g. of 2 to 5 carbon atoms, for example, cyanomethyl); alkenyl (e.g. of 2 to 5 carbon atoms such as 2-propenyl); alkynyl (e.g. of 2 to 5 carbon atoms such as 2-propynyl); alkoxyalkyl (e.g. of 2 to 8 carbon atoms, for example, 2-methoxyethyl); amino; alkylamino (e.g. of 1 to 6 carbon atoms); alkoxy (e.g. of 1 to 6, preferably 1 to 4, carbon atoms); haloalkenyl or haloalkynyl; or alkylthioalkyl (e.g. of 2 to 8 carbon atoms, for example 2-methylthioethyl) or the corresponding alkylsulfinylalkyl or alkylsulfonylalkyl groups (having, respectively 1 or 2 oxygen atoms on the S atom); and Ar is an aryl radical. Ar is further defined by the limitation that the 3-Methyl-4-Difluoromethyl Analogs of the compounds of this invention are herbicides, said Analogs being compounds which are otherwise identical to compounds of this invention except that said Analogs have, at the 3- and 4-positions of the 4,5-dihydrotriazol-(1H)-ring, a $CH_3$ and a $CHF_2$ substituent, respectively. The aryl radical thus represents a group useful in the 1-aryl-4,5-dihydro-1,2,4-triazol-5(1H)-one art to give herbicidal compounds when attached at the 1-position of an appropriate known 4,5-dihydro-1,2,4-triazol-5(1H)-one. For instance any of the aryl radicals of the aforementioned patents may be used.

The Ar radical is preferably such that said 3-Methyl-4-Difluoromethyl Analog has marked herbicidal properties. For instance, the 3-Methyl-4-Difluoromethyl Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species: velvetleaf (*Abutilon theophrasti*), green foxtail (*Setaria viridis*); Modes: pre-emergent, post-emergent. Testing for such herbicidal activity may be carried out in the manner described below (under the heading "Herbicidal Activity").

Ar is preferably a ring-substituted aryl radical. For instance it may have a benzene ring such as the radical indicated by the following formula

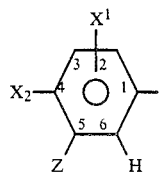

wherein $X^1$ may be for instance hydrogen or halogen, preferably fluorine or chlorine, the halogen atom advantageously being positioned at the C-2 carbon atom of the phenyl ring;

$X^2$ may be hydrogen, halogen such as fluorine, chlorine, or bromine; alkyl of 1 to 6 (preferably 1 to 4) carbon atoms, particularly methyl, haloalkyl of 1 to 5 carbon atoms, for example, trifluoromethyl, alkoxy of 1 to 6 (preferably 1 to 4) carbon atoms;

Z may, for instance, be hydrogen; halogen such as fluorine, chlorine, or bromine; alkyl of 1 to 6 (preferably 1 to 4) carbon atoms; cyanoalkyl; haloalkyl of 1 to 5 carbon atoms; nitro; a group —OR; or a group —CO—$R^6$ or $CH_2CO$—$R^6$ or $CH(CH_3)CO$—$R^6$; or a group —$OSO_2R^9$;

R may be hydrogen, alkyl of 1 to 6 (preferably 1 to 4) carbon atoms which may be substituted with cycloalkyl of 3 to 7 carbon atoms (for example, methyl or 1-methylethyl, or cyclohexylmethyl), cycloalkyl of 3 to 7 carbon atoms which may be substituted with alkyl of 1 to 6 carbon atoms (for example, cyclopentyl or methylcyclopropyl), alkoxyalkyl of 2 to 8 carbon atoms (for example, ethoxymethyl), cyanoalkyl of 2 to 7 carbon atoms such as cyanomethyl or 2-cyanoethyl, alkenyl of 2 to 5 carbon atoms such as 2-propenyl, alkynyl of 2 to 5 carbon atoms such as 2-propynyl, haloalkyl of 1 to 5 (preferably 1 to 3) carbon atoms especially a fluoroalkyl, haloalkenyl of 2 to 5 carbon atoms, haloalkynyl of 2 to 5 carbon atoms such as 3-bromo-2-propynyl, alkylsulfonyl of 1 to 6 (preferably 1 to 4) carbon atoms (wherein the alkyl moiety may be substituted with halogen, especially fluorine or chlorine, cyano, alkoxy or alkylthio of 1 to 4 carbon atoms such as methoxy or methylthio, or alkylamino or dialkylamino in which each alkyl is of 1 to 4 carbon atoms), alkylaminosulfonyl or dialkylaminosulfonyl wherein each alkyl is of 1 to 4 carbon atoms, arylsulfonyl such as phenylsulfonyl, alkylcarbonyl of 2 to 7 carbon atoms such as acetyl, or a 5- or 6-membered ring heterocyclic group of 1 or 2 same or different heteroatoms selected from O, S (including the S-oxide and S-dioxide), and N or an alkyl radical of 1 to 5 (preferably 1 to 3) carbon atoms substituted with said heterocyclic group. R may also be a group —$CR^3R^4(CH_2)_n$—CO—$Q^1$—$R^5$ in which n is 0 to 2 (preferably 0); $R^3$ and $R^4$ may be independently hydrogen or alkyl or alkoxy of 1 to 4 carbon atoms, $Q^1$ is O, S or $NR^7$ wherein $R^7$ may be H or alkyl of 1 to 6 (preferably 1 to 4) carbon atoms and $R^5$ may be hydrogen, alkyl of 1 to 6 (preferably 1 to 4) carbon atoms, alkoxyalkyl or alkylthioalkyl of 2 to 6 carbon atoms, haloalkyl of 1 to 5 carbon atoms (especially fluoroalkyl or chloroalkyl), alkenyl of 2 to 5 carbon atoms such as 2-propenyl, cycloalkenyl of 5 to 7 carbon atoms which may be substituted with alkyl of 1 to 4 carbon atoms (for example, 2-cyclohexenyl), cyclohexenylalkyl of 6 to 10 carbon atoms (for example, 3-cyclohexenylmethyl), phenyl or benzyl (which may be ring-substituted with fluorine, chlorine, bromine, or alkyl, alkoxy, or alkylthio of 1 to 4 carbon atoms), cyanoalkyl of 2 to 7 carbon atoms such as cyanomethyl, alkynyl of 2 to 5 carbon atoms such as 2-propynyl, alkylideneamino of 1 to 6 (preferably 1 to 4) carbon atoms which may be substituted with cycloalkyl 3 to 7 carbon atoms, cycloalkylideneamino of 5 to 7 carbon atoms which may be substituted with alkyl of 1 to 4 carbon atoms. When $Q^1$ is $NR^7$, $R^5$ may additionally be alkoxy, alkylthio, or alkylsulfonyl, each of 1 to 6 carbon atoms, phenylsulfonyl, or phenylalkylsulfonyl of 1 to 3 alkyl carbon atom.

As indicated above, R of the —OR substituent may be a heterocyclic group or an alkyl radical substituted with a heterocyclic group. The R group of this type may be any of those disclosed in my now abandoned copending application Ser. No. 655,960, filed Sept. 28, 1984, and its abandoned parent application Ser. No. 541,596, filed Oct. 13, 1983, which disclose aryltriazolinones whose aryl groups have such —OR substituents (the present application is a continuation-in-part of both those applications and incorporates, by reference, their entire disclosures.) The disclosures in said applications are found in U.S. Pat. No. 4,702,763 which is a continuation-in-part under 37 CFR 1.62 of application Ser. No. 655,960. The "Ar" radical of this invention may be any of the aryl radicals disclosed in those applications. Among the R groups, on those aryl radicals, which may be employed are 1-methyl-3-pyrrolidinyl, furfuryl or 2-thienylmethyl, or preferably 3-tetrahydrofuranyl, tetrahydrofurfuryl, tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran-4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahydrothien-3-yl, 2,2-dimethyl-1,1,3,3-tetraoxo-1,3-dithiolan-4-ylmethyl, 1,4-dithiacycloheptan-6-yl, 1,4-dithiacyclohept-5-ene-6-yl, tetrahydro-4H-pyran-3-yl, glycidyl, 2,3-epithiopropyl, 2,2-bis(chlorodifluoromethyl)-1,3-dioxolan-4-ylmethyl, or 1,1-dioxotetrahydro-4H-thiopyran-4-yl.

As indicated above, Z may be a group $-CO-R^6$, $-CH_2CO-R^6$ or $-CH(CH_3)CO-R^6$ where $R^6$ is hydroxy, alkoxy or alkylthio of 1 to 6 carbon atoms such as methoxy or methylthio, alkoxyalkoxy of 2 to 6 carbon atoms (for example, 2-methoxyethoxy), amino, or alkylamino or dialkylamino wherein each alkyl is of 1 to 6 (preferably 1 to 4) carbon atoms and may be substituted with alkoxy of 1 to 4 carbon atoms (for example, methylamino, dimethylamino, or (methyl)(2-methoxyethyl)amino).

As indicated above R of the —OR substituent may be a group $-CR^3R^4(CH_2)_nCOQ^1-R^5$. Aryl triazolinones whose aryl radicals have such —OR substituents of this type are disclosed in my copending application Ser. No. 666,933 filed Oct. 31, 1984. (The present application is a continuation-in-part of that application, whose entire disclosure is incorporated herein by reference.) The "Ar" radical of this invention may be any of the aryl radicals disclosed in that copending application.

As indicated above Z may also be a group $-OSO_2R^9$ where $R^9$ is alkyl, haloalkyl, cyanoalkyl, arylalkyl, cyclic alkyl, alkenyl, haloalkenyl, arylalkenyl, alkynyl, haloalkynyl, arylalkynyl, aryl, or a group of the formula $-(CH_2)_mNR^{3'}R^{4'}$ or -alkyl-Y—$R^{5'}$ wherein m is 0 to 5; $R^{3'}$ is hydrogen or alkyl; $R^{4'}$ is alkyl or a group of the formula -alkyl-$Y^{3'}-R^{8'}$; $R^{8'}$ is alkyl, alkoxycarbonylalkyl, alkenyl, or alkynyl; and $Y^{3'}$ is oxygen or S(O)$_r$ in which r is 0 to 2. My now abandoned copending application Ser. No. 650,755 filed Sept. 13, 1984 and its abandoned parent application Ser. No. 533,013 filed Sept. 15, 1983 (of both of which this application is a continuation-in-part, the entire disclosure of said copending applications being incorporated herein by reference) disclose aryl triazolinones whose aryl groups have a 5-substituent designated in said applications as "—O-SO$_2$R". The disclosures in said applications are found in U.S. Pat. No. 4,705,557 which is a continuation-in-part under 37 CFR 1.62 of application Ser. No. 650,755. The "Ar" radical of this invention may be any of the aryl radicals disclosed in those applications. Among the —OSO$_2$R$^9$ groups, on those aryl radicals, which may be used are those in which $R^9$ is methyl, ethyl, propyl, 1-methylethyl, butyl, 2-methylpropyl, 1-methylpropyl, 3-methylbutyl, chloromethyl, dichloromethyl, 3-chloropropyl, bromomethyl, difluoromethyl, trifluoromethyl, cyanomethyl, benzyl, cyclopropyl, 2-propenyl, 2,3,3-trichloro-2-propenyl, 2-propynyl, 3-bromo-2-propynyl, dimethylamino, dimethylaminoethyl, 2-methoxyethyl, 2-ethoxyethyl, 2-(2-propenoxy)ethyl, 2-(2-propenthio)ethyl, 2-(2-propynoxy)ethyl, 2-(methoxycarbonylmethoxy)ethyl, and 2-(methoxycarbonylmethylthio)ethyl.

Frequently, the aryl radical will be a dihalophenyl radical, preferably a 2,4-dihalophenyl radical, for example, a 5-(alkoxy or alkynyloxy of up to 6 carbon atoms) -2,4-dihalophenyl radical such as a 4-chloro-2-fluoro-5-(1-methylethoxy)phenyl or 4-chloro-2-fluoro-5-(2-propynyloxy)phenyl radical.

It will be understood that any alkyl, alkenyl or alkynyl groups of the compound may be straight chain or branched chain radicals. Thus, 1-methylethyl, 2-methyl-2-propenyl, and 1-methyl-2-propynyl are branched chain examples of alkyl, alkenyl, and alkynyl radicals respectively. The halogen may be fluorine, chlorine, bromine or iodine. The haloalkyl radical may have one or more same or different halogen atoms.

Included in the genus above are compounds in which Z is hydroxy, which, while generally herbicidal at high application rates, are more useful as intermediates than as herbicides. As useful intermediates in the preparation of the more herbicidally active members of the genus, such compounds form a preferred embodiment of the invention.

With respect to herbicidal properties, in the embodiments presently of most interest, the substituents $X^1$ and $X^2$ are preferably both halogen, with $X^1$ being fluorine or chlorine and $X^2$ being chlorine or bromine. The $X^1$ halogen will usually be positioned at the C-2 carbon atom of the phenyl ring. The compounds wherein $X^1$ is fluorine are particularly preferred.

The present compounds may be prepared by methods described in the literature or by methods analogous and similar thereto and within the skill of the art.

To make the compounds of the present invention in which $R^2$ is CHF$_2$, it is particularly convenient to start with CHF$_2$COOH, by converting the latter into an ester of difluoroacetylcarbamic acid (e.g. an ester of the formula CHF$_2$—CO—NHCO—O-lower alkyl), as by first converting the starting material into its acid chloride (e.g. by reaction with SOCl$_2$) and then reacting the latter with a lower alkyl urethane of the formula NH$_2$CO—O-lower alkyl as illustrated in Step A of Example 1, below.

The ester of difluoroacetylcarbamic acid may then be converted into a 1-aryl-4,5-dihydro-3-difluoromethyl-1,2,4-triazol-5(1H)-one by reacting it with an aryl hydrazine, as illustrated in Step B of Example 1. The aryl group of that hydrazine may carry all the substituents desired in the final compound (as is the case in the process for making compound 10 described at the end of Step B of Example 1) or those substituents, and any R$^1$ substituent, may be added in subsequent reactions, as illustrated in Steps C, D, E, F and G of Example 1. One or both of the (halogen) substituents at the 2- and/or 4-position of the phenyl group may be introduced subsequently, e.g. by halogenating (as with SO$_2$Cl$_2$) a 1-aryl-4,5-dihydro-3-difluoromethyl-4-methyl-1,2,4-triazol-5(1H)-one having hydrogen at one of those 2- and/or 4-positions and having any appropriate group at the 5-position of the phenyl group.

Instead of the alkyl difluoroacetylcarbamate one may use a haloacetonitrile (such as $F_2HC-CN$ or $F_3C-CN$ or $F_2ClC-CN$) for reaction with the aryl hydrazine (as illustrated in Step A of Example 2, below) to form the polyhaloacetamidine, which may then be reacted with phosgene to form a 1-aryl-4,5-dihydro-3-polyhalomethyl-4,5-dihydro-1,2,4-triazol-5(1H)-one (as illustrated in Step B of Example 2). Subsequent reactions may add an $R^1$ substituent at the 4-position of the 4,5-dihydro-1,2,4-triazol ring (as in Step C of Example 2) and/or vary the substituents on the aryl radical.

In these synthesis methods (e.g. the particular routes described above and in the Examples) there are formed useful intermediates which are 1-aryl-4,5-dihydro-1,2,4-triazol-5(1H)-ones having H on the nitrogen at the 4-position of the 4,5-dihydrotriazol ring and haloalkyl of 1 to 4 carbon atoms (e.g. $CHF_2$, $CF_3$ or $CClF_2$) on the carbon at the 3-position of that ring. (It will be understood that these compounds may also exist in their tautomeric forms as 1-aryl-1,2-dihydro-1,2,4-triazol-5(1H)-ones having hydrogen on the nitrogen at the 2-position. The 1-aryl group of such an intermediate may be a substituted phenyl radical identical with that present in the final compound or it may be a substituted phenyl radical containing an easily replaceable substituent (e.g., a methoxy group at the 5-position of the phenyl radical, as in a 5-methoxy-4-chloro(or bromo)-2-fluorophenyl radical) which phenyl radical can then be converted, by replacing that substituent, to the final substituted phenyl radical, preferably after first converting it to the corresponding phenolic radical (e.g. a 5-hydroxyphenyl radical). When the aryl group is to have a 2-F substituent it is preferred that the F substituent be present before formation of the heterocyclic ring, e.g. by using a fluorophenyl hydrazine as the reactant.

Some representative compounds of this invention are identified in the following table.

TABLE 1

| Cmpd No. | $X^1$ | $X^2$ | Z | $R^2$ | $R^1$ |
|---|---|---|---|---|---|
| 1 | Cl | Cl | OH | $CHF_2$ | $CHF_2$ |
| 2 | Cl | Cl | OH | $CHF_2$ | $CH_3$ |
| 3 | H | H | $OCH_3$ | $CHF_2$ | $CHF_2$ |
| 4 | H | H | $OCH_3$ | $CHF_2$ | $CH_3$ |
| 5 | Cl | Cl | $OCH_3$ | $CHF_2$ | $CHF_2$ |
| 6 | Cl | Cl | $OCH_3$ | $CHF_2$ | $CH_3$ |
| 7 | Cl | Cl | $OCH_2C\equiv CH$ | $CHF_2$ | $CH_3$ |
| 8 | Cl | Cl | $OCH_2C\equiv CH$ | $CHF_2$ | $CHF_2$ |
| 9 | Cl | Cl | O—(1,3-dioxolan-2-yl) | $CHF_2$ | $CHF_2$ |
| 10 | Cl | Cl | $OCH(CH_3)_2$ | $CHF_2$ | H |
| 11 | Cl | Cl | $OCH(CH_3)_2$ | $CHF_2$ | $CH_3$ |
| 12 | Cl | Cl | $OCH(CH_3)_2$ | $CHF_2$ | $CH_2CH=CH_2$ |
| 13 | Cl | Cl | $OCH_2C\equiv CH$ | $CHF_2$ | $CH_2CH=CH_2$ |
| 14 | Cl | Cl | $OCH(CH_3)CO_2C_2H_5$ | $CHF_2$ | $CH_3$ |
| 15 | Cl | Cl | $OCH(CH_3)CO_2C_2H_5$ | $CHF_2$ | $CH_2CH=CH_2$ |
| 16 | Cl | Cl | $OCH_2CO_2CH_3$ | $CHF_2$ | $CH_3$ |
| 17 | Cl | Cl | $OCH_2CN$ | $CHF_2$ | $CH_3$ |
| 18 | Cl | Cl | $OCH_2CONH_2$ | $CHF_2$ | $CH_3$ |
| 19 | Cl | Cl | O—(1,3-dioxolan-2-yl) | $CHF_2$ | $CH_3$ |
| 20 | F | Cl | $OCH_2C\equiv CH$ | $CHF_2$ | $CH_3$ |
| 21 | F | Cl | $OCH(CH_3)CO_2C_2H_5$ | $CHF_2$ | $CH_3$ |
| 22 | F | Cl | $OCH_3$ | $CHF_2$ | $CH_3$ |
| 23 | F | Cl | OH | $CHF_2$ | $CH_3$ |
| 24 | Cl | Cl | $OCH(CH_3)_2$ | $CClF_2$ | $CH_3$ |
| 25 | Cl | Cl | $OCH_2C\equiv CH$ | $CClF_2$ | $CH_3$ |
| 26 | Cl | Cl | $OCH(CH_3)CO_2C_2H_5$ | $CClF_2$ | $CH_3$ |
| 27 | Cl | Cl | $OCH(CH_3)_2$ | $CHF_2$ | $C_2H_5$ |
| 28 | Cl | Cl | OH | $CHF_2$ | $C_2H_5$ |
| 29 | Cl | Cl | $OCH_2C\equiv CH$ | $CHF_2$ | $C_2H_5$ |
| 30 | F | Cl | $OCH_3$ | $CClF_2$ | H |
| 31 | F | Cl | $OCH_3$ | $CClF_2$ | $CH_3$ |
| 32 | F | Cl | $OCH_2OCH_3$ | $CHF_2$ | $CH_3$ |
| 33 | F | Cl | $OCH_3$ | $CHF_2$ | $CH_2OCH_3$ |
| 34 | F | Cl | $OCH_2C\equiv CH$ | $CHF_2$ | $CH_2CN$ |
| 35 | Cl | Cl | $OCH(CH_3)_2$ | $CF_3$ | $CH_3$ |
| 36 | Cl | Cl | $OCH(CH_3)_2$ | $CF_3$ | H |
| 37 | Cl | Cl | $OCH_2C\equiv CH$ | $CF_3$ | $CH_3$ |

TABLE 1-continued

| Cmpd No. | X¹ | X² | Z | R² | R¹ |
|---|---|---|---|---|---|
| 38 | Cl | Cl | OH | $CF_3$ | $CH_3$ |
| 39 | F | Cl | OCH(CH₃)CONHSO₂-(2-Cl-phenyl) | $CHF_2$ | $CH_3$ |
| 40 | F | Cl | OCH(CH₃)CO₂C(CH₃)₃ | $CF_2$ | $CH_3$ |
| 41 | F | Cl | OCH(CH₃)₂ | $CHF_2$ | $CH_3$ |
| 42 | F | Cl | OCH₂SCH₃ | $CHF_2$ | $CH_3$ |
| 43 | F | Cl | OCH₂CN | $CHF_2$ | $CH_3$ |
| 44 | F | Cl | OCHF₂ | $CHF_2$ | $CH_3$ |
| 45 | F | Cl | OCH(CH₃)C≡CH | $CHF_2$ | $CH_3$ |
| 46 | F | Cl | OCH₂C≡CH | $CClF_2$ | $CH_3$ |
| 47 | F | Cl | OCH(CH₃)₂C≡CH | $CHF_2$ | $CH_3$ |
| 48 | F | Cl | OCH₂C≡CH | $CF_3$ | $CH_3$ |
| 49 | F | Cl | OCH₂C≡CH | $CF_2Cl$ | $CH_3$ |
| 50 | F | Cl | OCH₂CN | $CF_3$ | $CH_3$ |
| 51 | F | Cl | OCH₂CN | $CF_2Cl$ | $CH_3$ |
| 52 | F | Cl | OCH(CH₃)C≡CH | $CF_3$ | $CH_3$ |
| 53 | F | Cl | OCH₂C≡CH | $CF_2CF_3$ | $CH_3$ |
| 54 | Cl | Cl | OCH₂CN | $CF_3$ | $CH_3$ |
| 55 | F | Cl | OCH₂CN | $CF_2CF_3$ | $CH_3$ |
| 56 | F | CH₃ | OCH₂C≡CH | $CHF_2$ | $CH_3$ |
| 57 | Cl | CH₃ | OCH₂C≡CH | $CHF_2$ | $CH_3$ |
| 58 | F | Cl | OCH(CH₃)₂ | $CF_3$ | $CH_3$ |
| 59 | F | Cl | (3-tetrahydrofuranyloxy) | $CHF_2$ | $CH_3$ |
| 60 | F | Cl | OSO₂CH₃ | $CHF_2$ | $CH_3$ |
| 61 | F | Cl | OSO₂CHCl₂ | $CHF_2$ | $CH_3$ |
| 62 | F | Cl | OCH₂-(2-tetrahydrofuranyl) | $CHF_2$ | $CH_3$ |
| 63 | F | Cl | OCH₂C(Cl)=CH₂ | $CHF_2$ | $CH_3$ |
| 64 | F | Cl | OCH₂C(Cl)=CCl₂ | $CHF_2$ | $CH_3$ |
| 65 | F | Cl | OSO₂CF₃ | $CHF_2$ | $CH_3$ |
| 66 | F | Cl | OSO₂CH(CH₃)₂ | $CHF_2$ | $CH_3$ |
| 67 | F | Cl | OCH₂C≡CH | $CHF_2$ | $CH_2OCH_3$ |
| 68 | F | Cl | OCH₂C≡CH | $CHF_2$ | $CH_2CH=CH_2$ |
| 69 | F | Cl | OCH₂-(2,2-dimethyl-1,3-dioxolan-4-yl) | $CHF_2$ | $CH_3$ |
| 70 | F | Cl | OCH₂-(2,2-dichlorocyclopropyl) | $CHF_2$ | $CH_3$ |
| 71 | Cl | Cl | OCH(CH₃)CH₂OCH₃ | $CHF_2$ | $CH_3$ |
| 72 | F | Cl | OCH₂-(1,3-dioxolan-2-yl) | $CHF_2$ | $CHF_2$ |

TABLE 1-continued

Structure: aryl group with X¹ (ortho), X² (para), Z (meta) substituents; attached via N-N to C(=O)-N(R¹)-C(=CR²)

| Cmpd No. | X¹ | X² | Z | R² | R¹ |
|---|---|---|---|---|---|
| 73 | F | Cl | (tetrahydrofuran-3-yloxy, with SO₂) | CF₃ | CH₂CH=CH₂ |
| 74 | F | Cl | OSO₂CH₂CH₂OCH₃ | CHF₂ | CH₃ |
| 75 | F | Cl | OSO₂N(CH₃)₂ | CF₃ | CH₂CH₃ |
| 76 | F | Cl | OCH₂CH=CH₂ | CHF₂ | CH₂SCH₃ |
| 77 | F | Cl | OCH₂OCH₃ | CHF₂ | CH₂SO₂CH₃ |
| 78 | F | Cl | OCH₂C≡CH | CHF₂ | NH₂ |
| 79 | F | Cl | OCH₂C≡CH | CHF₂ | OCH₃ |
| 80 | F | Cl | OCH₂C≡CH | CHF₂ | NHCH₃ |
| 81 | Cl | CF₃ | OCH₂C≡CH | CHF₂ | CH₃ |
| 82 | F | OCH₃ | OCH(CH₃)₂ | CF₃ | CH₃ |
| 83 | F | Cl | OCH₂CO₂C₂H₅ | CHF₂ | CH₃ |
| 84 | F | Cl | OCH(CH₃)CO₂C₂H₅ | CF₃ | CH₃ |
| 85 | F | Cl | OCH(CH₃)CO₂C₂H₅ | CF₂Cl | CH₃ |
| 86 | F | Cl | OCH(CH₃)CO₂CH₂SCH₃ | CHF₂ | CH₃ |
| 87 | F | Cl | OCH(CH₃)CO₂—phenyl | CHF₂ | CH₃ |
| 88 | F | Cl | OCH(CH₃)CO₂—CH₂—(tetrahydrofuran-2-yl) | CHF₂ | CH₃ |
| 89 | F | Cl | OCH(CH₃)CO₂—C(CH₃)₂C≡CH | CHF₂ | CH₃ |
| 90 | F | Cl | OCH(CH₃)CO₂—C(CH₃)₂CN | CHF₂ | CH₃ |
| 91 | F | Cl | OCH(CH₃)CO₂CH(CH₃)₂ | CHF₂ | CH₃ |
| 92 | F | Cl | OCH(CH₃)CO₂CH₂CN | CHF₂ | CH₃ |
| 93 | F | Cl | OCH(CH₃)CO₂—(tetrahydrothiopyranyl, S) | CHF₂ | CH₃ |
| 94 | F | Cl | OCH(CH₃)CO₂C₂H₅ | CHF₂ | CH₂CN |
| 95 | F | Cl | OCH(CH₃)CO₂C₂H₅ | CHF₂ | CH₂OCH₃ |
| 96 | F | Cl | OCH(CH₃)CO₂OCH₂CH₂Cl | CHF₂ | CH₃ |
| 97 | F | Cl | OCH(CH₃)CO₂CH₂CH=CH₂ | CHF₂ | CH₃ |
| 98 | F | Cl | OCH(CH₃)CO₂CH₂—phenyl | CHF₂ | CH₃ |
| 99 | F | Cl | OCH(CH₃)COSC₂H₅ | CHF₂ | CH₃ |
| 100 | F | CH₃ | OCH(CH₃)CO₂CH₃ | CHF₂ | CH₃ |
| 101 | Br | Cl | OCH(CH₃)CO₂CH₃ | CHF₂ | CH₃ |
| 102 | F | Cl | OCH(CH₃)CO₂N=C(CH₃)₂ | CHF₂ | CH₃ |
| 103 | F | Cl | OCH(CH₃)CO₂CH₂CO₂CH₃ | CHF₂ | CH₃ |
| 104 | F | Cl | OCH(CH₃)COSCH₂CO₂C₂H₅ | CHF₂ | CH₃ |
| 105 | F | Cl | OCH(CH₃)CO₂H | CHF₂ | CH₃ |
| 106 | F | Cl | OCH(CH₃)CO₂Na | CHF₂ | CH₃ |
| 107 | F | Cl | OCH₂CONH₂ | CHF₂ | CH₃ |
| 108 | F | Cl | OCH(CH₃)CONHCH₃ | CHF₂ | CH₃ |
| 109 | F | Cl | OCH(CH₃)CONHCH₂C≡CH | CHF₂ | CH₃ |
| 110 | F | Cl | OCH(CH₃)CONHCH₂CH₂OCH₃ | CHF₂ | CH₃ |
| 111 | F | Cl | OCH(CH₃)CONHC(CH₃)₂CN | CHF₂ | CH₃ |
| 112 | F | Cl | OCH(CH₃)CON(CH₃)(OCH₃) | CHF₂ | CH₃ |
| 113 | F | Cl | OCH(CH₃)CONHCH₂CH=CH₂ | CHF₂ | CH₃ |
| 114 | F | CH₃ | OCH(CH₃)CON(CH₃)₂ | CHF₂ | CH₃ |

TABLE 1-continued

[Structure: X²-, X¹-, Z-substituted phenyl with N=N-C(=O)-N(R¹)-C(=NR²?)... hydrazide structure shown at top]

| Cmpd No. | X¹ | X² | Z | R² | R¹ |
|---|---|---|---|---|---|
| 115 | F | CH₃ | OCH(CH₃)CONHCH₃ | CHF₂ | CH₂CN |
| 116 | F | Cl | OCH(CH₃)CONH₂ | CHF₂ | CH₂OCH₃ |
| 117 | F | Cl | OCH(CH₃)CONHCH₂CO₂CH₃ | CHF₂ | CH₃ |
| 118 | F | Cl | OCH(CH₃)CONHCH₂CONH₂ | CHF₂ | CH₃ |
| 119 | F | Cl | OCH(CH₃)CON(CH₂CN)₂ | CHF₂ | CH₃ |
| 120 | F | Cl | OCH(CH₃)CONHSO₂CH₃ | CHF₂ | CH₃ |
| 121 | F | Cl | OCH(CH₃)CON(Na)SO₂CH₃ | CHF₂ | CH₃ |
| 122 | F | Cl | OCH(CH₃)CONHSO₂—C₆H₅ | CHF₂ | CH₃ |
| 123 | F | Cl | OCH(CH₃)CONHSO₂N(CH₃)₂ | CHF₂ | CH₃ |
| 124 | F | Cl | OCH(CH₃)CON(saccharinyl) | CHF₂ | CH₃ |
| 125 | F | Cl | OCH(CH₃)CONHSO₂—(2-CO₂CH₃-C₆H₄) | CHF₂ | CH₃ |
| 126 | F | Cl | OCH(CH₃)CON(morpholino) | CHF₂ | CH₃ |
| 127 | Br | Cl | OCH(CH₃)CONHCH₃ | CHF₂ | CH₃ |
| 128 | F | Cl | Cl | CHF₂ | CH₃ |
| 129 | F | Cl | CH₂CN | CHF₂ | CH₃ |
| 130 | F | Cl | CH₃ | CHF₂ | CH₃ |
| 131 | F | Cl | CH₂Cl | CHF₂ | CH₃ |
| 132 | F | Cl | NO₂ | CHF₂ | CH₃ |
| 133 | F | Cl | SO₃H | CHF₂ | CH₃ |
| 134 | F | Cl | CO₂H | CHF₂ | CH₃ |
| 135 | F | Cl | CO₂C₂H₅ | CHF₂ | CH₃ |
| 136 | F | Cl | CONHCH₃ | CHF₂ | CH₃ |
| 137 | F | Cl | CONHSO₂CH₃ | CHF₂ | CH₃ |
| 138 | F | Cl | COSC₂H₅ | CHF₂ | CH₃ |
| 139 | F | Cl | CO₂CH₂OCH₃ | CHF₂ | CH₃ |
| 140 | F | Cl | CONHSO₂—(4-CH₃-C₆H₄) | CHF₂ | CH₃ |
| 141 | F | Cl | CON(Na)SO₂—(4-CH₃-C₆H₄) | CHF₂ | CH₃ |
| 142 | F | Cl | CONHSO₂N(C₂H₅)₂ | CHF₂ | CH₃ |
| 143 | Cl | Cl | CO₂CH₃ | CHF₂ | CH₃ |
| 144 | F | CH₃ | CONHCH₃ | CHF₂ | CH₃ |
| 145 | F | Cl | CO₂C₂H₅ | CHF₂ | CH₂CN |
| 146 | F | Cl | CO₂C₂H₅ | CF₂Cl | CH₂OCH₃ |
| 147 | F | Cl | CONHCH₂C≡CH | CHF₂ | CH₃ |

TABLE 1-continued

[Structure: X¹, X² substituents on benzene ring with Z, linked to N-N=C(R²)-C(=O)-N(R¹) group]

| Cmpd No. | X¹ | X² | Z | R² | R¹ |
|---|---|---|---|---|---|
| 148 | F | Cl | CONHSO₂—(phenyl with Cl) | CHF₂ | CH₃ |
| 149 | F | Cl | CH₂CO₂CH₃ | CHF₂ | CH₃ |
| 150 | F | Cl | CH(CH₃)CO₂C₂H₅ | CHF₂ | CH₃ |
| 151 | F | Cl | CH(CH₃)CO₂H | CHF₂ | CH₃ |
| 152 | F | Cl | CH₂CO₂Na | CHF₂ | CH₃ |
| 153 | F | Cl | CH(CH₃)CONH₂ | CHF₂ | CH₃ |
| 154 | F | Cl | CH(CH₃)COSC₂H₅ | CHF₂ | CH₃ |
| 155 | F | Cl | CH₂CO₂CH₂CH₂OCH₃ | CF₃ | CH₃ |
| 156 | F | Cl | CH(CH₃)CONHC₂H₅ | CHF₂ | CHF₂ |
| 157 | F | Cl | CH(CH₃)CONHSO₂CF₃ | CHF₂ | CH₃ |
| 158 | F | Cl | CH(CH₃)CONHSO₂—(phenyl)—CH₃ | CHF₂ | CH₂CH=CH₂ |
| 159 | F | Cl | CH₂CONHSO₂N(CH₃)₂ | CHF₂ | CH₃ |
| 160 | Cl | Cl | CH(CH₃)CONHSO₂—(phenyl with Cl) | CHF₂ | CH₃ |
| 161 | F | Cl | NH—CH(CH₃)COOC₂H₅ | CHF₂ | CH₃ |
| 162 | F | Cl | NH—CH(CH₃)CON(C₂H₅)(OCH₃) | CHF₂ | CH₃ |

Other representative compounds are those which are identical with compounds 1-162 respectively, except that X¹ is F and X² is Br. Still other representative compounds are those which are identical with compounds 1-162 respectively, except that X¹ is F and X² is CF₃. Other representative compounds are those which are identical with compounds 1-126, 128-162 respectively except that X¹ is Br.

The following Examples illustrate the preparation of the compounds of this invention.

EXAMPLE 1

N-(2-Chlorophenylsulfonyl) 1-[2-Chloro-4-Fluoro-5-(3-Difluoromethyl-4,5-Dihydro-4-Methyl-5-Oxo-1H-1,2,4-Triazol-1-Yl)Phenoxy]-Propionamide

Step A

Ethyl difluoroacetylcarbamate

During a thirty minute period 65.4 g (0.55 mole) of thionyl chloride was added dropwise to 50.0 g (0.52 mole) of difluoroacetic acid with stirring, while maintaining a reaction temperature of 20°–25° C. After complete addition the mixture was stirred at room temperature for 1.5 hours and 46.4 g (0.52 mole) of urethane was added. The resultant mixture was heated at reflux for approximately three hours then allowed to cool to room temperature and stir for approximately 18 hours. The reaction mixture was again heated at 77° C. for two hours. Unreacted materials were removed from the reaction mixture by evaporation under reduced pressure leaving 81.1 g of ethyl difluoroacetylcarbamate as a semi-solid residue.

The nmr spectrum was consistent with the proposed structure.

Step B 1-(4-Chloro-2-fluoro-5-methoxyphenyl)-3-difluoromethyl-4,5-dihydro-1,2,4-triazol-5(1H)-one To a stirred mixture of 8.0 g (0.042 mole) of 4-chloro-2-fluoro-5-methoxyphenylhydrazine and 8.4 g (0.05 mole) of ethyl difluoroacetylcarbamate in 120 mL of xylene was added 2.1 g of phosphorus pentoxide. After complete addition the mixture was heated at reflux for one hour. While still hot, the reaction mixture was decanted from a dark residue into a clean flask. This residue was washed with xylene and the wash was combined with the decanted reaction mixture. The resultant mixture was stirred at room temperature for one hour. A precipitate formed and was removed by filtration and saved for later purification. The filtrate was extracted with three 150 mL portions of an aqueous 10% sodium hydroxide solution. The basic washes were combined and extracted with xylene. During the extraction an oil formed a third phase in the bottom of the separatory funnel and was removed from the other two phases. The basic aqueous phase was separated from the organic phase and filtered through a celite pad. The filtrate was washed with two portions of diethyl ether and acidified with concentrated hydrochloric acid. The acidified aqueous mixture was stirred at room temperature forming a brown precipitate. Collection of the precipitate by filtration yielded 1.5 g of 1-(4-chloro-2-fluoro-5-methoxyphenyl)-3-difluoromethyl-4,5-dihydro-1,2,4-triazol-5(1H)-one. The precipitate which was previously saved for purification was stirred in 70 mL of an aqueous 10% sodium hydroxide solution. The basic mixture was filtered through a celite pad to remove insoluble materials. The filtrate was acidified with concentrated hydrochloric acid producing a white solid. This solid was collected by filtration to yield an additional 0.7 g of product (mp 188°–190° C.).

The nmr spectrum was consistent with the proposed structure.

Compound 10, 1-[2,4-dichloro-5-(1-methylethoxy)-phenyl]-3-difluoromethyl-4,5-dihydro-1,2,4-triazol-5(1H)-one, and 1-(3-methoxyphenyl)-3-difluoromethyl-4,5-dihydro-1,2,4-triazol-5(1H)-one were prepared by the method of Example 1, Step B, from 2,4-dichloro-5-(1-methylethoxy)phenylhydrazine or 3-methoxyphenylhydrazine, respectively.

Step C 1-(4-chloro-2-fluoro-5-methoxyphenyl)-3-difluoromethyl-4,5-dihydro-4-methyl-1,2,4-triazol-5(1H)-one A stirred mixture of 2.0 g (0.0067 mole) of 1-(4-chloro-2-fluoro-5-methoxyphenyl)-3-difluoromethyl-4,5-dihydro-1,2,4-triazol-5(1H)-one and 2.1 g (0.015 mole) of potassium carbonate in 50 mL of acetone was heated at reflux for 30 minutes forming a thick slurry. Iodomethane (4.3 g, 0.03 mole) was added in one portion to the refluxing reaction mixture. After complete addition the mixture was stirred at reflux for 45 minutes. The mixture was cooled to room temperature and the solvent evaporated under reduced pressure leaving a solid residue. This residue was partitioned between water and methylene chloride. The two phase mixture was filtered through a celite pad. The organic phase was removed and was washed in succession with four portions of an aqueous 10% sodium hydroxide solution, and one portion each of an aqueous 10% hydrochloric acid solution, a saturated aqueous sodium carbonate solution, and water. After washing, the organic phase was dried over anhydrous magnesium sulfate and filtered. The filtrate was evaporated under reduced pressure to yield 1.6 g of 1-(4-chloro-2-fluoro-5-methoxyphenyl)-3-difluoromethyl-4,5-dihydro-4-methyl-1,2,4-triazol-5(1H)-one. A portion of this material was recrystallized from ethanol and water to provide the product as a light tan solid (mp 127°–129° C.), Compound 22.

The nmr spectrum was consistent with the proposed structure.

Analysis calcd for $C_{11}H_9ClF_3N_3O_2$: C 42.94; H 2.95; N 13.66; Found: C 42.74; H 3.15; N 13.35.

The following compounds were also prepared by the process of Example 1, Step C, from 1-(4-chloro-2-fluoro-5-methoxy-phenyl-3-difluoromethyl-4,5-dihydro-1,2,4-triazol-5(1H)-one; 1-(2,4-dichloro-5-methoxyphenyl)-3-difluoromethyl-4,5-dihydro-1,2,4-triazol-5(1H)-one; or 1-(3-methoxyphenyl)-3-difluoromethyl-4,5-dihydro-1,2,4-triazol-5(1H)-one and one of the following:

| Compound | Reagent |
|---|---|
| 4 | iodomethane |
| 6 | iodomethane |
| 11 | iodomethane |
| 12 | allyl bromide |
| 27 | iodoethane |
| 33 | chloromethyl methyl ether |

Compounds which contain a 4-difluoromethyl group (i.e. Compounds 3 and 5) may be prepared by a process analogous to Example 1, Step C, by reacting 1-(3-methoxyphenyl)-3-difluoromethyl-4,5-dihydro-1,2,4-triazol-5(1H)-one or 1-(2,4-dichloro-5-methoxyphenyl)-3-difluoromethyl-4,5-dihydro-1,2,4-triazol-5(1H)-one first with sodium hydroxide and tetrabutylammonium bromide in cyclohexane and tetrahydrofuran followed by chlorodifluoromethane.

Step D 1-(4-Chloro-2-fluoro-5-hydroxyphenyl)-3-difluoromethyl-4,5-dihydro-4-methyl-1,2,4-triazol-5(1H)-one To a stirred ice cold solution of 1.5 g (0.0048 mole) of 1-(4-chloro-2-fluoro-5-methoxyphenyl)-3-difluoromethyl-4,5-dihydro-4-methyl-1,2,4-triazol-5(1H)-one in 80 mL of methylene chloride was added dropwise 14.2 mL of a 1M solution of boron tribromide in methylene chloride. After complete addition the mixture was allowed to warm to room temperature and stir for approximately 18 hours. The mixture was poured into ice water and the resultant mixture stirred until the ice had melted. The organic phase was separated from the mixture and was washed with two portions of water. After washing, the organic phase was dried over anhydrous magnesium sulfate and filtered. Evaporation of the filtrate under reduced pressure yielded 1.2 g of 1-(4-chloro-2-fluoro-5-hydroxyphenyl)-3-difluoromethyl-4,5-dihydro-4-methyl-1,2,4-triazol-5(1H)-one (mp 153°–155° C.), Compound 23.

The nmr spectrum was consistent with the proposed structure.

Compounds 1, 2, 28 and 38 were prepared by the process disclosed in Example 1, Step D, from the corresponding 1-(2-halo-4-chloro-5-alkoxyphenyl)-1,2,4-triazol-5(1H)-one.

Step E tert-Butyl 2-[2-chloro-4-fluoro-5-(3-difluoromethyl-4,5-dihydro-4-methyl-5-oxo-1H-1,2,4-triazol-1-yl)phenoxy]propionate A mixture of 0.7 g (0.0023 mole) of 1-(4-chloro-2-fluoro-5-hydroxyphenyl)-3-difluoromethyl-4,5-dihydro-4-methyl-1,2,4-triazol-5(1H)-one, 0.9 g (0.0067 mole) of potassium carbonate, and 0.6 g (0.0027 mole) of tert-butyl 2-bromopropionate in 40 mL of acetone was stirred at room temperature for approximately 72 hours. The reaction mixture was partitioned between water and methylene chloride and the organic phase was washed with water. After drying over anhydrous magnesium sulfate the organic phase was filtered. Evaporation of the filtrate under reduced pressure yielded 0.9 g of tert-butyl 2-[2-chloro-4-fluoro-5-(3-difluoromethyl-4,5-dihydro-4-methyl-5-oxo-1H-1,2,4-triazol-1-yl)phenoxy]propionate as an oil, Compound 40.

The nmr spectrum was consistent with the proposed structure.

The following compounds were also prepared by the process of Example 1, Step E, from 1-(2,4-dichloro-5-hydroxyphenyl)-3-difluoromethyl-4,5-dihydro-4-methyl-1,2,4-triazol-5(1H)-one, Compound 2; 1-(4-chloro-2-fluoro-5-hydroxyphenyl)-3-difluoromethyl-4,5-dihydro-4-methyl-1,2,4-triazol-5(1H)-one, Compound 23; 1-(2,4-dichloro-5-hydroxyphenyl)-3-chlorodifluoromethyl-4,5-dihydro-4-methyl-1,2,4-triazol-5(1H)-one; 1-(2,4-dichloro-5-hydroxyphenyl)-3-trifluoromethyl-4,5-dihydro-4-methyl-1,2,4-triazol-5(1H)-one, Compound 38; 1-(2,4-dichloro-5-hydroxyphenyl)-4-ethyl-3-difluoromethyl-4,5-dihydro-1,2,4-triazol-5(1H)-one, Compound 28; 1-(2,4-dichloro-5-hydroxyphenyl)-3-difluoromethyl-4,5-dihydro-4-(2-propenyl)-1,2,4-triazol-5(1H)-one; or 1-(2,4-dichloro-5-hydroxyphenyl)-4-cyanomethyl-3-difluoromethyl-4,5-dihydro-1,2,4-triazol-5(1H)-one and one of the following:

| Compound | Reagent |
|---|---|
| 7 | propargyl bromide |
| 8 | propargyl bromide |
| 13 | propargyl bromide |
| 16 | methyl bromoacetate |
| 17 | bromo acetonitrile |
| 18 | iodoacetamide |
| 20 | propargyl bromide |
| 21 | ethyl 2-bromopropionate |
| 25 | propargyl bromide |
| 29 | propargyl bromide |
| 32 | chloromethyl methyl ether |
| 34 | propargyl bromide |
| 37 | propargyl bromide |

In addition, the following compounds were prepared in a manner analogous to Example 1, Step E, replacing potassium carbonate and acetone with sodium hydride and N,N-dimethylformamide, from one of the 1,2,4-triazol-5(1H)-one intermediates listed above and one of the following:

| Compound | Reagent |
|---|---|
| 9 | 3-tetrahydrofuryl 4-methylbenzenesulfonate |
| 14 | ethyl 2-bromopropionate |
| 15 | ethyl 2-bromopropionate |
| 19 | 3-tetrahydrofuryl 4-methylbenzenesulfonate |
| 26 | ethyl 2-bromopropionate |

Step F

2-[2-Chloro-4-fluoro-5-(3-difluoromethyl-4,5-dihydro-4-methyl-5-oxo-1H-1,2,4-triazol-1-yl)phenoxy]propionic acid A mixture of 0.8 g (0.002 mole) of tert-butyl 2-[2-chloro-4-fluoro-5-(3-difluoromethyl-4,5-dihydro-4-methyl-5-oxo-1H-1,2,4-triazol-1-yl)phenoxy]propionate and 59.2 g (0.52 mole) of trifluoroacetic acid was stirred at room temperature for two hours. Most of the trifluoroacetic acid was removed from the mixture by distillation under reduced pressure leaving a residue. This residue was partitioned between methylene chloride and water. The organic phase was dried over anhydrous magnesium sulfate and filtered. The filtrate was evaporated under reduced pressure to yield 0.5 g of 2-[2-chloro-4-fluoro-5-(3-difluoromethyl-4,5-dihydro-4-methyl-5-oxo-1H-1,2,4-triazol-1-yl)phenoxy]propionic acid as an oil.

The nmr was consistent with the proposed structure.

Step G

N-(2-Chlorophenylsulfonyl) 2-[2-chloro-4-fluoro-5-(3-difluoromethyl-4,5-dihydro-4-methyl-5-oxo-1H-1,2,4-triazol-1-yl)phenoxy]propionamide]

A stirred mixture of 0.4 g (0.0011 mole) of 2-[2-chloro-4-fluoro-5-(3-difluoromethyl-4,5-dihydro-4-methyl-5-oxo-1H-1,2,4-triazol-1-yl)phenoxy]propionic acid, 0.2 g (0.0011 mole) of 2-chlorophenylsulfonyl isocyanate and a catalytic amount (0.03 g) of 4-dimethylaminopyridine in 40 mL of toluene was heated at reflux for approximately 18 hours. The mixture was cooled and evaporated under reduced pressure to yield 0.5 g of N-(2-chlorophenylsulfonyl) 2-[2-chloro-4-fluoro-5-(3-difluoromethyl-4,5-dihydro-4-methyl-5-oxo-1H-1,2,4-triazol-1-ly)phenoxy]propionamide as a solid (mp 162°–166° C.), Compound 39.

The nmr spectrum was consistent with the proposed structure.

EXAMPLE 2

1-[2,4-Dichloro-5-(1-Methylethoxy)Phenyl]-3-Trifluoromethyl-4,5-Dihydro-4-Methyl-1,2,4-Triazol-5(1H)-One Step A N-[2,4-Dichloro-5-(1-methylethoxy)anilino]trifluoroacetamidine Under a dry nitrogen atmosphere a stirred solution of 2.4 g (0.01 mole) of 2,4-dichloro-5-(1-methylethoxy)phenylhydrazine in 140 mL of methanol was cooled to −60° C. in a dry ice-isopropanol bath. Trifluoroacetonitrile (23.2 g, 0.24 mole) was bubbled into the cold solution during a two minute period. After complete addition the cold solution was stirred for 30 minutes, then allowed to warm slowly to room temperature during the next three hours. A stream of nitrogen gas was bubbled into the room temperature solution to aid in the vaporization and removal of trifluoroacetonitrile, leaving a liquid residue. This residue was evaporated further under reduced pressure to leave a resinous material. This material was stirred in cold pentane to produce a solid. The pentane was decanted and the solid triturated in fresh cold pentane. The pentane was decanted and the solid dried under reduced pressure to yield 2.9 g of N-[2,4-dichloro-5-(1-methylethoxy)anilino]trifluoroacetamidine (mp 80.5°–81° C.).

The nmr spectrum was consistent with the proposed structure.

In addition to the above intermediate, N-[2,4-dichloro-5-(1-methylethoxy)anilino]chlorodifluoroacetamidine and N-(4-chloro-2-fluoro-5-methoxyanilino)chlorodifluoroacetamidine were prepared by the process described in Example 2, Step A, from the correspondingly substituted phenylhydrazine and chlorodifluoroacetonitrile.

Step B

1-[2,4-Dichloro-5-(1-methylethoxy)phenyl]-3-trifluoromethyl-4,5-dihydro-1,2,4-triazol-5(1H)-one Under a dry nitrogen atmosphere a stirred solution of 2.1 g (0.0062 mole) of N-[2,4-dichloro-5-(1-methylethoxy)anilino]trifluoroacetamidine in 130 mL of toluene was cooled in an ice bath. To this was added 5.2 mL (0.037 mole) of triethylamine followed by the dropwise addition of 45.6 mL of a 2.9% (0.013 mole) phosgene in toluene solution. After complete addition the mixture was heated quickly to 65° C. and stirred at that temperature for 45 minutes. The mixture was allowed to cool to room temperature and stir for approximately 18 hours. The mixture was diluted with 25 mL of water and stirred vigorously for a brief period. Sufficient concentrated hydrochloric acid was added to make the aqueous phase acidic (pH 2). The acidic aqueous phase and the organic phase were shaken briskly after which the organic phase was separated from the mixture and saved for further purification. The aqueous phase was extracted with methylene chloride and the extract evaporated to leave a yellow solid. This solid was dissolved in toluene and the resultant solution added to the saved organic phase from above. The combined organic phase was stirred at room temperature with decolorizing carbon and filtered through a celite pad. The filtrate was extracted with a 1N sodium hydroxide solution. This extract was washed with toluene and acidified with concentrated hydrochloric acid to pH 2. Sodium chloride was added to the acidic solution to the point of saturation. A precipitate formed upon cooling this solution and was collected by filtration. The filter cake was rinsed with several portions of ice cold water and dried under reduced pressure to yield 1.8 g of 1-[2,4-dichloro-5-(1-methylethoxy)phenyl]-3-trifluoromethyl-4,5-dihydro-1,2,4-triazol-5(1H)-one (mp 160°–161° C.), Compound 36.

The nmr was consistent with the proposed structure.

Analysis calc'd for $C_{12}H_{10}Cl_2F_3N_3O_2$: C 40.47; H 2.83; N 11.80; Found: C 39.01; H 2.96; N 11.38.

Also prepared by the process of Example 2, Step B, were 1-[2,4-dichloro-5-(1-methylethoxy)phenyl]-3-chlorodifluoromethyl-4,5-dihydro-1,2,4-triazol-5(1H)-one and 1-(4-chloro-2-fluoro-5-methoxyphenyl)-3-chlorodifluoromethyl-4,5-dihydro-1,2,4-triazol-5(1H)-one (Compound 30) from the correspondingly substituted chlorodifluoroacetamidine.

Step C

1-[2,4-Dichloro-5-(1-methylethoxy)phenyl]-3-trifluoromethyl-4,5-dihydro-4-methyl-1,2,4-triazol-5(1H)-one Under a dry nitrogen atmosphere 0.1 g (0.0038 mole) of dry sodium hydride was added to a stirred solution of 1.3 g (0.0035 mole) of 1-[2,4-dichloro-5-(1-methylethoxy)phenyl]-3-trifluoromethyl-4,5-dihydro-1,2,4-triazol-5(1H)-one in 30 mL of N,N-dimethylformamide. The mixture was stirred at room temperature for 20 minutes and 0.6 g (0.0038 mole) of iodomethane was added. After complete addition the mixture was warmed to 65° C. and stirred at that temperature for one hour. The mixture was allowed to cool to room temperature and stir for approximately 18 hours. Most of the solvent was removed by distillation under reduced pressure to leave a liquid residue. This residue was partitioned between water and diethyl ether. The organic phase was washed first with a 2N sodium hydroxide solution followed by water. The organic solution was dried over an anhydrous magnesium sulfate and filtered. The filtrate was evaporated under reduced pressure to yield 1.2 g of 1-[2,4-dichloro-5-(1-methylethoxy)phenyl]-3-trifluoromethyl-4,5-dihydro-4-methyl-1,2,4-triazol-5(1H)-one as a solid (mp 96°–98° C.), Compound 35.

The nmr spectrum was consistent with the proposed structure.

Analysis calc'd for $C_{13}H_{12}Cl_2F_3N_3O_2$: C 42.18; H 3.27; N 11.35; Found: C 41.52; H 3.18; N 11.14.

Compound 31 was prepared by the manner of Example 1, Step C, from Compound 30. Compound 24 was prepared in an analogous manner from 1-[2,4-dichloro-5-(1-methylethoxy)phenyl]-3-chlorodifluoromethyl-4,5-dihydro-1,2,4-triazol-5(1H)-one using potassium carbonate and acetone in place of sodium hydride and N,N-dimethylformamide.

Characterizing properties of some of the compounds of the invention are given in the following Table.

TABLE 2

| Cmpd. No. | Melting Point (°C.) | Empirical Formula | Elemental Analysis C | H | N |
|---|---|---|---|---|---|
| 1 | Solid | $C_{10}H_5Cl_2F_4N_3O_2$ | | | |
| 2 | 190–192 | $C_{10}H_7Cl_2F_2N_3O_2$ | C 38.73<br>F 38.74 | 2.27<br>2.26 | 13.55<br>13.31 |
| 3 | 86–88 | $C_{11}H_9F_4N_3O_2$ | | | |
| 4 | 113–115 | $C_{11}H_{11}F_2N_3O_2$ | | | |
| 5 | 131–138 | $C_{11}H_7Cl_2F_4N_3O_2$ | | | |
| 6 | 156–159 | $C_{11}H_9Cl_2F_2N_3O_2$ | | | |
| 7 | 121–124 | $C_{13}H_9Cl_2F_2N_3O_2$ | | | |
| 8 | Solid | $C_{13}H_7Cl_2F_4N_3O_2$ | | | |
| 9 | Oil | $C_{14}H_{11}Cl_2F_4N_3O_3$ | | | |
| 10 | Solid | $C_{12}H_{11}Cl_2F_2N_3O_2$ | | | |
| 11 | 95–97 | $C_{13}H_{13}Cl_2F_2N_3O_2$ | | | |
| 12 | 81–83 | $C_{15}H_{15}Cl_2F_2N_3O_2$ | | | |
| 13 | 69–74 | $C_{15}H_{11}Cl_2F_2N_3O_2$ | | | |
| 14 | Oil | $C_{15}H_{15}Cl_2F_2N_3O_4$ | | | |
| 15 | Oil | $C_{17}H_{17}Cl_2F_2N_3O_4$ | | | |
| 16 | Solid | $C_{13}H_{11}Cl_2F_2N_3O_4$ | | | |
| 17 | 132–135 | $C_{12}H_8Cl_2F_2N_4O_2$ | | | |
| 18 | 190–193.5 | $C_{12}H_{10}Cl_2F_2N_4O_2$ | | | |
| 19 | Oil | $C_{14}H_{13}Cl_2F_2N_3O_3$ | | | |
| 20 | 106–107 | $C_{13}H_9ClF_3N_3O_2$ | C 47.08<br>F 46.98 | 2.73<br>2.80 | 12.67<br>12.61 |
| 21 | Oil | $C_{15}H_{15}ClF_3N_3O_4$ | | | |
| 22 | 127–129 | $C_{11}H_9ClF_3N_3O_2$ | C 42.94<br>F 42.74 | 2.95<br>3.15 | 13.66<br>13.35 |
| 23 | 153–155 | $C_{10}H_7ClF_3N_3O_2$ | | | |
| 24 | 69–72 | $C_{13}H_{12}Cl_3F_2N_3O_2$ | C 40.39<br>F 40.92 | 3.13<br>3.28 | 10.87<br>10.96 |
| 25 | 146–147.5 | $C_{13}H_8Cl_3F_2N_3O_2$ | C 40.81<br>F 40.48 | 2.11<br>2.04 | 10.98<br>10.61 |
| 26 | Oil | $C_{15}H_{14}Cl_3F_2N_3O_4$ | | | |
| 27 | Oil | $C_{14}H_{15}Cl_2F_2N_3O_2$ | | | |
| 28 | 120–124 | $C_{11}H_9Cl_2F_2N_3O_2$ | | | |
| 29 | 104–107 | $C_{14}H_{11}Cl_2F_2N_3O_2$ | C 46.43<br>F 46.85 | 3.06<br>3.10 | 11.60<br>11.54 |
| 30 | 200–205 | $C_{10}H_6Cl_2F_3N_3O_2$ | C 36.61<br>F 37.33 | 1.84<br>2.16 | 12.81<br>12.63 |
| 31 | 78–88 | $C_{10}H_8Cl_2F_3N_3O_2$ | | | |
| 32 | 114–116 | $C_{12}H_{11}ClF_3N_3O_3$ | | | |
| 33 | Solid | $C_{12}H_{11}ClF_3N_3O_3$ | | | |
| 34 | Oil | $C_{14}H_8ClF_3N_4O_2$ | | | |
| 35 | 96–98 | $C_{13}H_{12}Cl_2F_3N_3O_2$ | C 42.18<br>F 41.52 | 3.27<br>3.18 | 11.35<br>11.14 |
| 36 | 160–161.5 | $C_{12}H_{10}Cl_2F_3N_3O_2$ | C 40.47<br>F 39.01 | 2.83<br>2.96 | 11.80<br>11.38 |
| 37 | 132.5–134.5 | $C_{13}H_8Cl_2F_3N_3O_2$ | C 42.63<br>F 42.83 | 2.20<br>2.54 | 11.48<br>10.70 |
| 38 | 174–175 | $C_{10}H_6Cl_2F_3N_3O_2$ | C 36.61<br>F 38.24 | 1.84<br>2.14 | 12.81<br>12.10 |
| 39 | 162–166 | $C_{19}H_{15}Cl_2F_3N_4O_5S$ | | | |
| 40 | Oil | $C_{17}H_{19}ClF_3N_3O_4$ | | | |

HERBICIDAL ACTIVITY

The plant tests species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), field bindweed (*Convolvulus arvensis*), morningglory (*Ipomea lacunosa* or *Ipomea hederacea*, velvetleaf (*Abutilon theophrasti*), barnyardgrass (*Echinochloa crus*

*galli*), green foxtail (*Setaria viridis*), johnsongrass (*Sorghum halepense*), yellow nutsedge (*Cyperus esculentus*), and rice (*Oryza sativa*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8–10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Alabama, 1977. The present rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in the tables below. The test compounds are identified in the tables below by numbers which correspond to those used above.

In the Tables of herbicidal data below "kg/ha" is kilograms per hectare.

TABLE 3

| Pre-emergence Herbicidal Activity | | | | |
|---|---|---|---|---|
| | % Control | | | |
| Compound No. | 1 | 2 | 3 | 4 |
| Rate (Kg/ha) | 8.0 | 8.0 | 8.0 | 8.0 |
| Species | | | | |
| COTTON | 100 | 100 | 0 | 10 |
| SOYBEAN | 100 | 60 | 0 | 20 |
| FIELD CORN | 90 | 90 | 0 | 0 |
| RICE | — | — | — | — |
| WHEAT | 90 | 90 | 0 | 0 |
| FIELD BINDWEED | 100 | 100 | 0 | 20 |
| MORNINGGLORY | 100 | 90 | 0 | 70 |
| VELVETLEAF | 100 | 100 | 0 | 90 |
| BARNYARDGRASS | 100 | 90 | 0 | 70 |
| GREEN FOXTAIL | 100 | 100 | 0 | 100 |
| JOHNSONGRASS | 100 | 90 | 0 | 70 |
| YELLOW NUTSEDGE | — | — | — | — |
| Compound No. | 5 | 6 | 7 | 8 |
| Rate (Kg/ha) | 2.0 | 2.0 | 2.0 | 2.0 |
| Species | | | | |
| COTTON | 50 | 100 | 100 | 100 |
| SOYBEAN | 70 | 90 | 100 | 100 |
| FIELD CORN | 100 | 100 | 100 | 100 |
| RICE | 90 | 100 | 100 | 100 |
| WHEAT | 100 | 100 | 100 | 100 |
| FIELD BINDWEED | 70 | 80 | 100 | 100 |
| MORNINGGLORY | 80 | 100 | 100 | 100 |
| VELVETLEAF | 100 | 100 | 100 | 100 |
| BARNYARDGRASS | 100 | 100 | 100 | 100 |
| GREEN FOXTAIL | 100 | 100 | 100 | 100 |
| JOHNSONTAIL | 100 | 100 | 100 | 100 |
| YELLOW NUTSEDGE | 90 | 100 | 90 | 90 |
| Compound No. | 9 | 10 | 11 | 12 |
| Rate (Kg/ha) | 2.0 | 2.0 | 1.0 | 1.0 |
| Species | | | | |
| COTTON | 90 | 10 | 60 | 40 |
| SOYBEAN | 100 | 0 | 100 | 60 |
| FIELD CORN | 100 | 70 | 90 | 80 |
| RICE | 100 | — | 80 | 30 |
| WHEAT | 100 | 0 | 90 | 40 |
| FIELD BINDWEED | 90 | 30 | 90 | 50 |
| MORNINGGLORY | 100 | 50 | 90 | 80 |
| VELVETLEAF | 100 | 70 | 100 | 100 |
| BARNYARDGRASS | 100 | 60 | 100 | 100 |
| GREEN FOXTAIL | 100 | 40 | 100 | 100 |
| JOHNSONGRASS | 100 | 80 | 100 | 90 |
| YELLOW NUTSEDGE | 90 | — | 80 | 20 |
| Compound No. | 13 | 14 | 15 | 16 |
| Rate (Kg/ha) | 2.0 | 2.0 | 2.0 | 1.0 |
| Species | | | | |
| COTTON | 100 | 100 | 90 | 60 |
| SOYBEAN | 100 | 30 | 0 | 0 |
| FIELD CORN | 90 | 40 | 70 | 0 |
| RICE | 90 | 80 | 40 | 10 |
| WHEAT | 90 | 80 | 80 | 0 |
| FIELD BINDWEED | 100 | 100 | 100 | 60 |
| MORNINGGLORY | 100 | 80 | 100 | 70 |
| VELVETLEAF | 100 | 100 | 100 | 10 |
| BARNYARDGRASS | 100 | 100 | 100 | 60 |
| GREEN FOXTAIL | 100 | 100 | 100 | 10 |
| JOHNSONGRASS | 100 | 100 | 90 | 40 |
| YELLOW NUTSEDGE | 80 | 100 | 80 | 20 |
| Compound No. | 17 | 18 | 19 | 20 |
| Rate (Kg/ha) | 1.0 | 1.0 | 1.0 | 0.125 |
| Species | | | | |
| COTTON | 100 | 40 | 100 | 100 |
| SOYBEAN | 60 | 10 | 90 | 100 |
| FIELD CORN | 100 | 80 | 100 | 100 |
| RICE | 100 | 30 | 100 | 100 |
| WHEAT | 100 | 0 | 100 | 100 |

TABLE 3-continued

Pre-emergence Herbicidal Activity

| | | | | |
|---|---|---|---|---|
| FIELD BINDWEED | 90 | 90 | 70 | 100 |
| MORNINGGLORY | 100 | 100 | 100 | 100 |
| VELVETLEAF | 100 | 90 | 100 | 100 |
| BARNYARDGRASS | 100 | 80 | 100 | 100 |
| GREEN FOXTAIL | 100 | 100 | 100 | 100 |
| JOHNSONGRASS | 100 | 70 | 100 | 100 |
| YELLOW NUTSEDGE | 90 | 30 | 100 | 90 |

| Compound No. | 21 | 22 | 23 | 24 |
|---|---|---|---|---|
| Rate (Kg/ha) | 1.0 | 1.0 | 8.0 | 1.0 |
| Species | | | | |
| COTTON | 80 | 80 | 100 | 0 |
| SOYBEAN | 10 | 100 | 100 | 60 |
| FIELD CORN | 40 | 100 | 100 | 90 |
| RICE | 70 | 100 | — | 60 |
| WHEAT | 80 | 100 | 100 | 70 |
| FIELD BINDWEED | 80 | 100 | 100 | 60 |
| MORNINGGLORY | 80 | 100 | 100 | 10 |
| VELVETLEAF | 100 | 100 | 100 | 60 |
| BARNYARDGRASS | 100 | 100 | 100 | 100 |
| GREEN FOXTAIL | 100 | 100 | 100 | 100 |
| JOHNSONGRASS | 70 | 100 | 100 | 100 |
| YELLOW NUTSEDGE | 100 | 100 | — | 0 |

| Compound No. | 25 | 26 | 27 | 28 |
|---|---|---|---|---|
| Rate (Kg/ha) | 0.5 | 2.0 | 1.0 | 2.0 |
| Species | | | | |
| COTTON | 20 | 50 | 20 | 10 |
| SOYBEAN | 70 | 50 | 20 | 10 |
| FIELD CORN | 100 | 30 | 90 | 90 |
| RICE | 60 | 80 | 70 | 30 |
| WHEAT | 40 | 20 | 80 | 30 |
| FIELD BINDWEED | 100 | 100 | 50 | 10 |
| MORNINGGLORY | 50 | 90 | 80 | 20 |
| VELVETLEAF | 100 | 100 | 100 | 20 |
| BARNYARDGRASS | 100 | 100 | 100 | 70 |
| GREEN FOXTAIL | 100 | 90 | 100 | 100 |
| JOHNSONGRASS | 90 | 40 | 100 | 90 |
| YELLOW NUTSEDGE | 60 | 50 | 60 | 10 |

| Compound No. | 29 | 30 | 31 | 32 |
|---|---|---|---|---|
| Rate (Kg/ha) | 0.5 | 8.0 | 0.5 | 0.5 |
| Species | | | | |
| COTTON | 40 | 0 | 30 | 90 |
| SOYBEAN | 100 | 0 | 60 | 100 |
| FIELD CORN | 100 | 0 | 90 | 100 |
| RICE | 80 | — | 70 | 100 |
| WHEAT | 100 | 0 | 90 | 100 |
| FIELD BINDWEED | 100 | 0 | 20 | 100 |
| MORNINGGLORY | 60 | 0 | 20 | 100 |
| VELVETLEAF | 100 | 0 | 100 | 100 |
| BARNYARDGRASS | 100 | 0 | 100 | 100 |
| GREEN FOXTAIL | 100 | 0 | 100 | 100 |
| JOHNSONGRASS | 100 | 0 | 60 | 100 |
| YELLOW NUTSEDGE | 70 | — | 80 | 100 |

| Compound No. | 33 | 34 | 35 | 36 |
|---|---|---|---|---|
| Rate (Kg/ha) | 1.0 | 0.5 | 1.0 | 8.0 |
| Species | | | | |
| COTTON | 90 | 80 | 20 | 0 |
| SOYBEAN | 80 | 90 | 30 | 0 |
| FIELD CORN | 100 | 90 | 90 | 0 |
| RICE | 90 | 80 | 60 | — |
| WHEAT | 100 | 90 | 50 | 0 |
| FIELD BINDWEED | 100 | 90 | 80 | 0 |
| MORNINGGLORY | 90 | 90 | 80 | 0 |
| VELVETLEAF | 100 | 100 | 100 | 0 |
| BARNYARDGRASS | 100 | 100 | 100 | 0 |
| GREEN FOXTAIL | 100 | 100 | 100 | 0 |
| JOHNSONGRASS | 100 | 90 | 100 | 0 |
| YELLOW NUTSEDGE | 90 | 70 | 20 | — |

| Compound No. | 37 | 39 | 40 |
|---|---|---|---|
| Rate (Kg/ha) | 1.0 | 1.0 | 2.0 |
| Species | | | |
| COTTON | 80 | 100 | 100 |
| SOYBEAN | 100 | 70 | 70 |
| FIELD CORN | 100 | 70 | 100 |
| RICE | 95 | 90 | 95 |
| WHEAT | 100 | 70 | 100 |
| FIELD BINDWEED | 100 | 100 | 100 |
| MORNINGGLORY | 100 | 100 | 95 |
| VELVETLEAF | 100 | 100 | 100 |
| BARNYARDGRASS | 100 | 100 | 100 |
| GREEN FOXTAIL | 100 | 100 | 100 |
| JOHNSONGRASS | 100 | 95 | 100 |
| YELLOW NUTSEDGE | 60 | 100 | 100 |

TABLE 4

Post-emergence Herbicidal Activity

| | % Control | | | |
|---|---|---|---|---|
| Compound No. | 1 | 2 | 3 | 4 |
| Rate (Kg/ha) | 8.0 | 8.0 | 8.0 | 8.0 |
| Species | | | | |
| COTTON | 100 | 100 | 40 | 10 |
| SOYBEAN | 90 | 90 | 0 | 20 |
| FIELD CORN | 100 | 90 | 0 | 0 |
| RICE | — | — | — | — |
| WHEAT | 100 | 100 | 0 | 0 |
| FIELD BINDWEED | 100 | 100 | 0 | 10 |
| MORNINGGLORY | 100 | 100 | 0 | 0 |
| VELVETLEAF | 100 | 100 | 0 | 0 |
| BARNYARDGRASS | 100 | 100 | 0 | 10 |
| GREEN FOXTAIL | 100 | 100 | 80 | 0 |
| JOHNSONGRASS | 100 | 100 | 30 | 20 |
| YELLOW NUTSEDGE | — | — | — | — |

| Compound No. | 5 | 6 | 7 | 8 |
|---|---|---|---|---|
| Rate (Kg/ha) | 2.0 | 2.0 | 2.0 | 2.0 |
| Species | | | | |
| COTTON | 100 | 80 | 100 | 100 |
| SOYBEAN | 100 | 90 | 100 | 100 |
| FIELD CORN | 100 | 100 | 100 | 100 |
| RICE | 100 | 100 | 100 | 100 |
| WHEAT | 100 | 100 | 100 | 100 |
| FIELD BINDWEED | 90 | 100 | 100 | 100 |
| MORNINGGLORY | 80 | 100 | 100 | 100 |
| VELVETLEAF | 100 | 100 | 100 | 100 |
| BARNYARDGRASS | 100 | 100 | 100 | 100 |
| GREEN FOXTAIL | 100 | 100 | 100 | 100 |
| JOHNSONGRASS | 100 | 100 | 100 | 100 |
| YELLOW NUTSEDGE | 100 | 100 | 90 | 80 |

| Compound No. | 9 | 10 | 11 | 12 |
|---|---|---|---|---|
| Rate (Kg/ha) | 2.0 | 8.0 | 1.0 | 1.0 |
| Species | | | | |
| COTTON | 100 | 40 | 100 | 100 |
| SOYBEAN | 100 | 20 | 90 | 70 |
| FIELD CORN | 100 | 40 | 100 | 80 |
| RICE | 100 | — | 90 | 30 |
| WHEAT | 100 | 0 | 100 | 90 |
| FIELD BINDWEED | 100 | 100 | 100 | 90 |
| MORNINGGLORY | 100 | 0 | 100 | 100 |
| VELVETLEAF | 100 | 80 | 100 | 100 |
| BARNYARDGRASS | 100 | 0 | 100 | 100 |
| GREEN FOXTAIL | 100 | 40 | 100 | 100 |
| JOHNSONGRASS | 100 | 0 | 100 | 90 |
| YELLOW NUTSEDGE | 80 | — | 60 | 0 |

| Compound No. | 13 | 14 | 15 | 16 |
|---|---|---|---|---|
| Rate (Kg/ha) | 2.0 | 2.0 | 2.0 | 1.0 |
| Species | | | | |
| COTTON | 100 | 100 | 100 | 60 |
| SOYBEAN | 100 | 50 | 60 | 40 |
| FIELD CORN | 100 | 70 | 100 | 40 |
| RICE | 90 | 80 | 100 | 10 |
| WHEAT | 100 | .80 | 100 | 0 |
| FIELD BINDWEED | 100 | 100 | 100 | 100 |
| MORNINGGLORY | 100 | 80 | 80 | 80 |
| VELVETLEAF | 100 | 100 | 100 | 100 |
| BARNYARDGRASS | 100 | 100 | 80 | 100 |
| GREEN FOXTAIL | 100 | 100 | 100 | 100 |
| JOHNSONGRASS | 100 | 100 | 80 | 40 |
| YELLOW NUTSEDGE | 70 | 70 | 50 | 0 |

| Compound No. | 17 | 18 | 19 | 20 |
|---|---|---|---|---|

TABLE 4-continued

Post-emergence Herbicidal Activity

| Rate (Kg/ha) | 1.0 | 1.0 | 1.0 | 0.125 |
|---|---|---|---|---|
| Species | | | | |
| COTTON | 100 | 50 | 90 | 100 |
| SOYBEAN | 60 | 20 | 80 | 80 |
| FIELD CORN | 90 | 20 | 90 | 100 |
| RICE | 30 | 10 | 100 | 100 |
| WHEAT | 100 | 10 | 100 | 100 |
| FIELD BINDWEED | 100 | 100 | 100 | 100 |
| MORNINGGLORY | 100 | 90 | 100 | 100 |
| VELVETLEAF | 100 | 100 | 100 | 100 |
| BARNYARDGRASS | 100 | 80 | 100 | 100 |
| GREEN FOXTAIL | 100 | 100 | 100 | 100 |
| JOHNSONGRASS | 100 | 60 | 100 | 100 |
| YELLOW NUTSEDGE | 90 | 0 | 90 | 80 |

| Compound No. | 21 | 22 | 23 | 24 |
|---|---|---|---|---|
| Rate (Kg/ha) | 1.0 | 1.0 | 8.0 | 1.0 |
| Species | | | | |
| COTTON | 100 | 100 | 100 | 100 |
| SOYBEAN | 50 | 100 | 90 | 40 |
| FIELD CORN | 70 | 100 | 100 | 30 |
| RICE | 90 | 100 | — | 10 |
| WHEAT | 100 | 100 | 100 | 10 |
| FIELD BINDWEED | 100 | 100 | 100 | 90 |
| MORNINGGLORY | 100 | 100 | 100 | 60 |
| VELVETLEAF | 100 | 100 | 100 | 100 |
| BARNYARDGRASS | 90 | 100 | 100 | 90 |
| GREEN FOXTAIL | 100 | 100 | 100 | 90 |
| JOHNSONGRASS | 90 | 90 | 100 | 50 |
| YELLOW NUTSEDGE | 90 | 100 | — | 0 |

| Compound No. | 25 | 26 | 27 | 28 |
|---|---|---|---|---|
| Rate (Kg/ha) | 0.5 | 2.0 | 1.0 | 0.5 |
| Species | | | | |
| COTTON | 100 | 100 | 90 | 90 |
| SOYBEAN | 80 | 50 | 70 | 30 |
| FIELD CORN | 70 | 20 | 80 | 30 |
| RICE | 40 | 70 | 90 | 40 |
| WHEAT | 30 | 30 | 80 | 20 |
| FIELD BINDWEED | 100 | 100 | 80 | 30 |
| MORNINGGLORY | 100 | 90 | 70 | 20 |
| VELVETLEAF | 100 | 90 | 100 | 70 |
| BARNYARDGRASS | 30 | 60 | 80 | 10 |
| GREEN FOXTAIL | 90 | 80 | 100 | 100 |
| JOHNSONGRASS | 30 | 20 | 90 | 70 |
| YELLOW NUTSEDGE | 20 | 40 | 10 | 10 |

| Compound No. | 29 | 30 | 31 | 32 |
|---|---|---|---|---|
| Rate (Kg/ha) | 0.5 | 8.0 | 0.5 | 0.5 |
| Species | | | | |
| COTTON | 90 | 30 | 90 | 100 |
| SOYBEAN | 50 | 10 | 70 | 100 |
| FIELD CORN | 90 | 10 | 60 | 100 |
| RICE | 40 | — | 40 | 100 |
| WHEAT | 60 | 10 | 60 | 100 |
| FIELD BINDWEED | 90 | 30 | 90 | 100 |
| MORNINGGLORY | 90 | 30 | 70 | 100 |
| VELVETLEAF | 100 | 10 | 100 | 100 |
| BARNYARDGRASS | 70 | 10 | ND | 100 |
| GREEN FOXTAIL | 90 | 20 | 90 | 100 |
| JOHNSONGRASS | 80 | 10 | 20 | 100 |
| YELLOW NUTSEDGE | 50 | — | 70 | 100 |

| Compound No. | 33 | 34 | 35 | 36* |
|---|---|---|---|---|
| Rate (Kg/ha) | 1.0 | 0.5 | 1.0 | 8.0 |
| Species | | | | |
| COTTON | 80 | 90 | 80 | 0 |
| SOYBEAN | 70 | 80 | 70 | 30 |
| FIELD CORN | 80 | 100 | 60 | 20 |
| RICE | 50 | 90 | 30 | — |
| WHEAT | 80 | 50 | 60 | 20 |
| FIELD BINDWEED | 70 | 90 | 80 | 0 |
| MORNINGGLORY | 100 | 70 | 80 | 20 |
| VELVETLEAF | 100 | 100 | 100 | 0 |
| BARNYARDGRASS | 90 | 30 | 90 | 20 |
| GREEN FOXTAIL | 100 | 80 | 90 | 0 |
| JOHNSONGRASS | 80 | 50 | 80 | 20 |
| YELLOW NUTSEDGE | 40 | 40 | 20 | — |

| Compound No. | 37 | 39 | 40 |
|---|---|---|---|
| Rate (Kg/ha) | 1.0 | 1.0 | 2.0 |
| Species | | | |
| COTTON | 100 | 100 | 100 |
| SOYBEAN | 95 | 90 | 95 |
| FIELD CORN | 100 | 100 | 100 |
| RICE | 95 | 50 | 90 |
| WHEAT | 95 | 95 | 100 |
| FIELD BINDWEED | 100 | 100 | 100 |
| MORNINGGLORY | 100 | 100 | 100 |
| VELVETLEAF | 100 | 100 | 100 |
| BARNYARDGRASS | 100 | 100 | 100 |
| GREEN FOXTAIL | 100 | 100 | 100 |
| JOHNSONGRASS | 100 | 100 | 100 |
| YELLOW NUTSEDGE | 70 | 95 | 100 |

*Data given are data for % Kill

For herbicidal application, the active compounds as above defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, water-soluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cotton seed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (Alachlor), 2-chloro-N-(2-ethyl-6-methylphenyl)-N-(2-methoxy-(1-methylethyl)acetamide (Metolachlor), and N-chloroacetyl-N-(2,6-diethylphenyl)glycine (Diethatyl-ethyl); benzothiadiazinone herbicides such as 3-(1-methylethyl)-(1H)-2,1,3-benzothiadiazin-4-(3H)-one-2,2-dioxide (Bentazon); triazine herbicides such as 6-chloro-N-ethyl-N-(1-methylethyl)-1,3,5-triazine-2,4-diamine (Atrazine), and 2-[4-chloro-6-(ethylamino)-1,3,5-triazin-2-yl]-amino-2-methylpropanenitrile (Cyanazine); dinitroaniline herbicides such as 2,6-dinitro-N,N-dipropyl-4-(trifluoromethyl)benzeneamine (Trifluralin); and aryl urea herbicides such as N'-(3,4-dichlorophenyl)-N,N-dimethylurea (Diuron) and N,N-dimethyl-N'-[3-(trifluoromethyl)phenyl]-urea (Fluometuron).

It is apparent that various modifications may be made in the formulation and application of the compounds of this invention, without departing from the inventive concepts herein, as defined in the following claims.

I claim:

1. An herbicidal compound of the formula

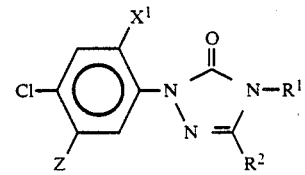

in which
X$^1$ is F or Cl;
Z is nitro or a group of the formula —OR, —CO—R$^6$, —CH$_2$CO—R$^6$, or —CH(CH$_3$)CO—R$^6$;
R is alkyl of 1 to 6 carbon atoms which is unsubstituted or is substituted with cycloalkyl or 3 to 7 carbon atoms, cycloalkyl of 3 to 7 carbon atoms which is unsubstituted or is substituted with alkyl of 1 to 6 carbon atoms, alkoxyalkyl of 2 to 8 carbon atoms, cyanoalkyl of 2 to 7 carbon atoms, alkenyl of 2 to 5 carbon atoms, alkynyl of 2 to 5 carbon atoms, haloalkyl of 1 to 5 carbon atoms, haloalkenyl of 2 to 5 carbon atoms, haloalkynyl of 2 to 5 carbon atoms, alkylsulfonyl of 1 to 6 carbon atoms (wherein the alkyl moiety is unsubstituted or is substituted with F, Cl, CN, alkoxy or alkylthio of 1 to 4 carbon atoms, or alkylamino or dialkylamino in which each alkyl is of 1 to 4 carbon atoms), alkylaminosulfonyl or dialkylaminosulfonyl in which each alkyl is of 1 to 4 carbon atoms, alkylcarbonyl of 2 to 7 carbon atoms, or a group of the formula —C(R$^3$) (R$^4$) (CH$_2$)$_n$—CO—Q$^1$R$^5$ or —C(R$^3$) (R$^4$) (CH$_2$)$_n$—CO—N(R$^7$) (R$^8$) in which n is 0 to 2;
R$^3$ and R$^4$ are independently H, alkyl of 1 to 4 carbon atoms, or alkoxy of 1 to 4 carbon atoms;
Q$^1$ is O or S;
R$^5$ is H, alkyl of 1 to 6 carbon atoms, alkoxyalkyl or alkylthioalkyl of 2 to 6 carbon atoms, haloalkyl of 1 to 5 carbon atoms, alkenyl of 2 to 5 carbon atoms, cycloalkenyl of 5 to 7 carbon atoms which is unsubstituted or is substituted with alkyl of 1 to 4 carbon atoms, cyclohexenylalkyl of 6 to 10 carbon atoms, phenyl or benzyl (which may be ring-substituted with fluorine, chlorine, bromine, or alkyl, alkoxy, or alkylthio of 1 to 4 carbon atoms), cyanoalkyl of 2 to 7 carbon atoms, alkynyl of 2 to 5 carbon atoms, alkylideneamino of 1 to 6 carbon atoms which is unsubstituted or is substituted with cycloalkyl 3 to 7 carbon atoms, or cycloalkylideneamino of 5 to 7 carbon atoms, which is unsubstituted or is substituted with alkyl of 1 to 4 carbon atoms;
R$^6$ is hydroxy, alkoxy or alkylthio of 1 to 6 carbon atoms, alkoxyalkoxy of 2 to 6 carbon atoms, amino, or alkylamino or dialkylamino wherein each alkyl is of 1 to 6 carbon atoms and is unsubstituted or is substituted with alkoxy of 1 to 4 carbon atoms;

$R^7$ is H or alkyl of 1 to 6 carbon atoms;

$R^8$ is $R^5$ or alkoxy of 1 to 6 carbon atoms, alkylthio of 1 to 6 carbon atoms, alkylsulfonyl of 1 to 6 carbon atoms, phenylsulfonyl, or phenylalkylsulfonyl of 1 to 3 alkyl carbon atoms;

$R^1$ is alkyl of 1 to 4 carbon atoms or haloalkyl of 1 to 3 carbon atoms; and $R^2$ is fluoroalkyl of 1 to 4 carbon atoms.

2. The compound of claim 1 wherein $R^1$ is $CH_3$ or $CHF_2$ and $R^2$ is $CHF_2$.

3. The compound of claim 2 wherein Z is —OR or —$CH(CH_3)CO$—$R^6$.

4. An herbicidal composition comprising an herbicidally effective amount of a compound of claim 1 in admixture with a suitable carrier.

5. A method for controlling undesired plant growth which comprises applying to the locus where control is desired an herbicidally effective amount of the composition of claim 4.

* * * * *